USD005536412A

United States Patent [19]
Ash

[11] Patent Number: 5,536,412
[45] Date of Patent: Jul. 16, 1996

[54] HEMOFILTRATION AND PLASMAFILTRATION DEVICES AND METHODS

[75] Inventor: Stephen R. Ash, Lafayette, Ind.

[73] Assignee: HemoCleanse, Inc., West Lafayette, Ind.

[21] Appl. No.: 180,080

[22] Filed: Jan. 11, 1994

Related U.S. Application Data

[63] Continuation-in-part of Ser. No. 832,080, Feb. 6, 1992, Pat. No. 5,277,820.

[51] Int. Cl.$^6$ .................. B01D 61/00; B01D 63/02; B01D 69/08
[52] U.S. Cl. .................. 210/645; 210/195.1; 210/195.2; 210/257.1; 210/258; 210/321.78; 210/321.87; 210/646; 210/650; 210/651; 210/660; 210/805; 604/4; 604/5; 604/6
[58] Field of Search .................. 210/644, 645, 210/646, 650, 651, 660, 767, 805, 195.1, 638, 195.2, 205, 321.78, 257.1, 257.2, 258, 321.72, 321.6, 433.1, 435, 321.87, 500.23; 604/4, 5, 6; 436/178; 422/101

[56] References Cited

U.S. PATENT DOCUMENTS

| | | | |
|---|---|---|---|
| 4,056,467 | 11/1977 | Christen et al. | 210/638 |
| 4,247,393 | 1/1981 | Wallace | 210/646 |
| 4,375,414 | 3/1983 | Strahilevitz | 210/638 |
| 4,661,246 | 4/1987 | Ash | 210/87 |
| 4,714,556 | 12/1987 | Ambrus et al. | 210/638 |
| 4,770,784 | 9/1988 | Davis et al. | 210/638 |
| 5,078,885 | 1/1992 | Matsumura | 210/638 |
| 5,211,850 | 5/1993 | Shettigar et al. | 210/646 |
| 5,328,614 | 7/1994 | Matsumura | 210/638 |

OTHER PUBLICATIONS

Ash, "Treatment of Acute Hepatic Failure with Encephalopathy: A Review", *Int. J. of Artif. Organs.*, vol. 14, pp. 191–195 (1991).

Winchester, "Hemoperfusion, in Replacement of Renal Function by dialysis" (Maher, ed.) Dordrecht; Kluwer Academic Publishers, PP. 439–459 (1989).

O'Grady et al., "Controlled Trials of Charcoal Hemoperfusion and Prognostic Factors in fulminant Hepatic Failure", *Gastroenterology*, vol. 94, pp. 1186–1192 (1988).

Dixit et al., "Restoration of Liver Function in Gunn Rats without Immunosuppression Using Transplanted Microencapsulated Hepatocytes, " *Hepatology*, vol. 12, pp. 1342–1349 (1990).

Dixit et al., "Cryopreserved Microencapsulated Hepatocytes—Transplantation Studies in Gunn Rats", *Transplantation*, vol. 55, pp. 616–622 (1993).

*Primary Examiner*—John Kim
*Attorney, Agent, or Firm*—Woodard, Emhardt, Naughton Moriarty & McNett

[57] ABSTRACT

Disclosed are preferred devices and methods which provide extracorporeal treatment of blood or other fluids for effective plasmafiltration or hemofiltration alone or in combination with dialysis.

10 Claims, 7 Drawing Sheets

HEMOFILTRATION AND PLASMAFILTRATION DEVICES AND METHODS

REFERENCE TO RELATED APPLICATION

This is a continuation-in-part application of U.S. patent application Ser. No. 07/832,080 filed Feb. 6, 1992, now U.S. Pat. No. 5,277,820.

BACKGROUND OF THE INVENTION

This invention generally relates to devices and methods for extracorporeally treating blood or blood fractions such as blood filtrate or plasma to selectively remove toxins therefrom.

By way of background, extensive efforts have been made to discover safe and effective methods for removing toxins from patients by extracorporeal treatment of their blood. These efforts have included many studies directed to methods for extracorporeal treatment of hepatic failure due to infection, cirrhosis, toxin damage or other causes. Many methods have been proposed with the goal of removing small molecular toxins, protein-bound molecules or larger molecules thought to be responsible for the coma and illness of hepatic failure. Thus far, evidence has been presented supporting adverse effects caused by non-protein bound small molecules such as ammonia, phenols, mercaptans, short chain fatty acids, aromatic amino-acids, neural inhibitors (GABA, glutamate), false neural transmitters (octopamine) and bile salts. Among these, phenols and mercaptans, along with bilirubin and bacterial endotoxins, also occur as strong protein-bound toxins and are thus more difficult to effectively remove from the blood. In addition, there are a variety of middle molecular weight toxins of liver failure having molecular weights of about 300 to about 10,000 which are difficult to effectively remove.

As to specific modes of treatment, those previously proposed and used have included blood perfusion over heterogeneous liver pieces or past membranes which contact hepatocytes. Also proposed and used have been hemoperfusion through columns of coated activated carbon or macroreticular resins, blood exchange, plasmapheresis with plasma replacement, plasmapheresis with plasma perfusion through bilirubin-binding and aromatic amino acid-binding sorbents, standard hemodialysis, standard hemodialysis with an amino acid dialysate and plasma exchange, high permeability hemodialysis, dialysis with charcoal-impregnated membranes, continuous hemofiltration, peritoneal dialysis, oral sorbents and many other therapies.

While some of these previously proposed treatments have produced neurological improvement in stage 2 or 3 coma and have aided hepatic regeneration after injury, they have not provided much clinical improvement in patients in stage 4 coma on respirators. Additionally, these diverse treatments each produce adverse effects on the patient, offsetting benefits. See, generally, Ash, S. R., Treatment of Acute Hepatic Failure With Encephalopathy: A Review, *Int. J. of Artif. Organs*, Vol. 14, pp. 191–195 (1991).

For example, although daily charcoal hemoperfusion has been shown to provide neurologic and physiologic improvement of patients with hepatic failure and coma, Winchester, J. F., Hemoperfusion, in Replacement of Renal Function by Dialysis (Maher, J. F., ed.), Dordrecht:Kluwer Academic Publishers, pp. 439–459, (1989), hemoperfusion nevertheless requires systemic anticoagulation and also depletes coagulation factors and platelets from the blood. Moreover, the relatively large sorbent granules used in hemoperfusion columns have limited surface area (about 1000–10,000 $m^2$). Consequently, the available sorbent surface area is saturated within a few hours, clearance of bound chemicals rapidly diminishes, and a new column must be used.

Furthermore, clinical benefits of charcoal hemoperfusion may be offset by deleterious effects of bio-incompatibility. In one instance, a controlled study of patients with fulminant hepatic failure, all treated with aggressive intensive care including intracerebral pressure monitoring, demonstrated that patients treated by hemoperfusion had a generally lower survival rates than those treated with aggressive intensive care alone. The only exception was noted in patients having fulminant hepatic failure due to hepatitis A or B, for whom there was reported a "trend toward improved survival" when treated with charcoal perfusion. O'Grady, J. G. et al., Controlled Trials of Charcoal Hemoperfusion and Prognostic Factors in Fulminant Hepatic Failure, *Gastroenterology*, Vol. 94, pp. 1186–92 (1988).

As mentioned, standard lemodialysis (i.e. dialysis of blood against only a dialysate solution) has also been studied as a possible treatment for hepatic failure. However, benefits of hemodialysis may be similarly obscured by removal of substances (e.g. urea) known not to be toxins of hepatic failure. Additionally, hemodialysis requires the use of large volumes of dialysate solution which limits the mobility and increases the complexity of the machines, or alternatively, it requires the provision of a sorbent column to "regenerate" the dialysate.

In light of this extensive background, there remain needs for improved devices and methods for the extracorporeal treatment of blood or of blood fractions to effectively remove toxins, including both soluble and protein-bound toxins. The present invention addresses these needs.

SUMMARY OF THE INVENTION

The present invention provides a unique filtration process (e.g. a hemofiltration or plasmafiltration process) which is highly effective in removing protein-bound and middle molecular weight toxins. The inventive process includes the steps of passing a fluid, such as blood, containing protein-bound or middle molecular weight blood toxins, through the interior of a hollow fiber membrane, and during the passage of blood, circulating a sorbent suspension against exterior surfaces of the hollow fiber membrane. As a further step, during the passage of blood and circulation of sorbent suspension, the plasma fraction of the blood is caused to alternately exit and re-enter the interior of the membrane. Thereby, blood plasma contacts the sorbent suspension upon exit from the interior of the membrane, so as to effectuate removal of the toxins from the blood. This embodiment of the invention is applied with preference to whole blood; however, the invention is not so limited, as it will be applicable as well to the treatment of other fluids containing middle molecular weight and/or protein bound blood toxins, e.g. blood fractions such as isolated blood plasma or other blood toxin-containing fluids such as blood filtrate.

Another preferred embodiment of the present invention provides a device which is highly effective for removing protein-bound or middle molecular weight toxins from fluids such as blood, blood plasma or blood filtrate. The preferred device of the invention includes a hollow fiber membrane, and a pump fluidly connected to the interior of the hollow fiber membrane and adapted to pass blood (or another fluid containing the toxins) through the interior. The device further includes a chamber surrounding the hollow fiber membrane, the chamber also being fluidly connected to a supply of sorbent suspension containing solid particulate adsorbent. A pump is adapted to circulate the sorbent suspension through the chamber and against exterior surfaces of the hollow fiber membrane. Means for causing the blood or other fluid or a fraction thereof passing through the interior of the membrane to alternately exit and re-enter the interior of the hollow fiber membrane are also provided.

Still another preferred embodiment of the present invention provides a method for circulating a sorbent suspension in a device for extracorporeal treatment of blood or a blood fraction. The method of the invention includes a step of providing the device having a sorbent circulation circuit and a blood circulation circuit separated by membranes, the membranes being compliantly formed to expand and contract in response to alternating positive pressure and negative pressure applied to the sorbent circulation circuit and thereby advance a sorbent suspension through the sorbent suspension circulation circuit. An accumulator reservoir is provided and fluidly connected to the sorbent circulation circuit, and is operable to alternately accumulate and expel sorbent suspension in response to alternating negative pressure and positive pressure applied to the accumulator reservoir. Thereby, the accumulator reservoir communicates the alternating negative and positive pressure to the sorbent circulation circuit. The method further includes applying alternating positive pressure and negative pressure to the accumulator reservoir so as to communicate the same to the sorbent circulation circuit and cause the compliant membranes to expand and contract, whereby the sorbent suspension is advanced through the sorbent suspension circuit.

Still another preferred embodiment of the invention provides a device for extracorporeal treatment of blood or a blood fraction. This device has a sorbent circulation circuit and a blood circulation circuit separated by membranes, wherein the membranes are compliantly formed to expand and contract in response to alternating positive pressure and negative pressure applied to the sorbent circulation circuit and thereby advance a sorbent suspension through the sorbent suspension circulation circuit. An accumulator reservoir is fluidly connected to the sorbent circulation circuit and operable to alternately accumulate and expel sorbent suspension in response to alternating negative pressure and positive pressure applied to the accumulator reservoir, the accumulator reservoir thereby communicating the alternating negative and positive pressure to the sorbent circulation circuit. The device also includes a source of positive pressure and of negative pressure fluidly connected to the accumulator reservoir. When alternating positive pressure and negative pressure are alternately applied to the accumulator reservoir, the same is communicated to the sorbent circulation circuit to cause the compliant membranes to expand and contract, whereby the sorbent suspension is advanced through the sorbent suspension circuit.

The invention thus provides methods and devices by which greater removal of protein-bound and middle molecular weight blood toxins from blood, blood plasma or blood filtrate can be achieved, and whereby efficient circulation of sorbents on the sorbent side of a variety of different types of extracorporeal treatment devices is effectuated. Additional objects, features and advantages of the present invention will be apparent from the description which follows.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, one preferred embodiment of this invention relates to a method which can be used for extracorporeal treatment of blood or a blood fraction by filtration, e.g. plasmafiltration (wherein plasma is filtered across a membrane) or hemofiltration (wherein middle molecular weight molecules (i.e. having molecular weights of about 300 to about 10,000) are filtered across a membrane), in a manner which provides the safe, consistent and effective removal of toxins, including protein-bound blood toxins and middle molecular weight blood toxins. This filtration can be used alone, or in connection with dialysis of the blood or blood fraction, for example using dialysis devices and methods as described in my prior U.S. patent application Ser. No. 07/832,080 filed Feb. 6, 1992, now U.S. Pat. No. 5,277,820, which is hereby incorporated by reference in its entirety. Likewise, the advantageous sorbent circulation system and method described in this prior application is effective to advance sorbent suspension through hollow fiber plasmafilters and hemofilters, and is generally applicable to advance sorbent suspension through a variety of extracorporeal treatment devices having blood and sorbent sides separated by a membrane, and thus also forms a part of the applicant's invention.

The sorbent suspension used in the invention can include powdered surface adsorptive agents, physiologic electrolytes and macromolecular flow inducing agents. In general, these components are present in effective amounts to achieve the desired removal of substances from and electrolyte balance in the blood of the patient while maintaining the stability and fluidity of the sorbent suspension. Because plasmafiltration membranes as used in the invention can potentially pass endotoxins, it is preferred that the sorbent suspension be free from measurable endotoxins. While general sorbent suspension production techniques have been sufficient for these purposes, if necessary, measures can be taken sanitize or sterilize the suspension, for example using heat or radiation (e.g. gamma-radiation), to assure that the sorbent suspension is substantially free from bacteria or other microbial growth which could potentially generate endotoxins or other harmful substances.

The powdered surface adsorptive agent can be any one of many known to those practiced in this area, but is preferably powdered activated charcoal. Further, the powdered surface adsorptive agent preferably has an average particle diameter of not greater than about 100 microns. More preferably, this average particle diameter is less than about 50 microns, with 90% or more of the particles having diameters not greater than about 75 microns. Particles exceeding 75 microns in diameter can be screened if necessary. As one example, a suitable finely powdered activated charcoal is available from American Norit Company, Inc. of Jacksonville, Fla. U.S.A., which can be screened to remove particles larger than those des i red.

The macromolecular flow inducing agents function to maintain the stability of the sorbent suspension formulation (i.e. helps to prevent solids from settling out of suspension) and maintain the flow properties of the suspension. One desirable flow inducing agent is a nonionic, hydroxyl-containing polymer such as a glycol derivative. Suitable agents of this type are available from BASF Wyandotte of Parsippany, N.J., U.S.A. under the trademark "Pluronic" polyols. These Pluronic polyols are polyoxyalkylene derivatives of propylene glycol. To date, applicant has used Pluronic F68, which functions both as a flow inducing agent and a defoaming agent. Another flow agent that has been included in preferred suspensions is macroreticular polyvinylpyrrolidone.

The types and amounts of electrolytes included in the suspension formulation will depend upon the specific needs of the patient and will be readily determinable by physicians or others skilled in the area. Typically, the electrolytes will include sodium and chloride (e.g. optionally provided as sodium chloride), and can also include bicarbonate, potassium, calcium, or any other electrolytes to be regulated in the patient. As indicated, however, the types and amounts of electrolytes may vary widely depending on patient needs.

The sorbent suspension formulation may also include ion-exchanger to bind ionic chemicals, e.g. ammonium, etc., which may occur in the patient's blood. Many suitable ion exchangers including both resins and other materials such as zeolites are known in the art. When included, the ion-exchanger is preferably a cation-exchange resin, which is desirably loaded with sodium or calcium. For example, to date, sodium polystyrene sulfonate has been a preferred material.

The surface adsorptive agent, electrolytes, flow inducing agents and any oilier additives will usually comprise about 5% to 30% by weight of the sorbent suspension formulation as a whole, with the remainder being water. Typically, solid sorbents will comprise about 2% to 25% by weight of the suspension formulation, and electrolytes will comprise about about 1% to 5% of the suspension formulation. Within these parameters, more preferred sorbent suspension formulations comprise about 2% to 20% powdered surface adsorptive agent, up to about 10% ion-exchanger, and up to about 1% flow agent such as a polyol and/or polyvinylpyrrolidone.

The sorbent suspension can also include viable hepatic cells, e.g. xenogenic or allogenic cells, alone or in combination with one or more of the solid adsorbents and other materials described above, to assist in the effective removal of toxins. For example, hepatocytes can be isolated from suitable donor tissue, purified and microencapsulated in polymer as described by Dixit et al., *Hepatology* 1990:12:1342. These microencapsulated cells can then be used directly in the sorbent suspension, or can be cryopreserved until use, for example as described by Dixit et al., *Transplantation* 1993; 55:616–22. When hepatic cells are so used, plasma is effectively separated from the blood by passage through the plasmafilter membrane, and proteins and toxins are convected into contact with the cells circulating exterior of the membrane. After the cells have acted upon the toxins, the plasma is returned through the membrane and back into the patient.

In connection with plasmafiltration or hemofiltration devices and methods, there are many suitable hollow fiber membranes which are known for use in plasmafiltration or hemofiltration of blood, and those skilled in the area will be readily able to select and utilize a suitable membranes in the present invention. Such membranes can be, for example, cellulosic membranes (e.g. cellulose acetates), and will have pore sizes sufficiently large to allow passage of plasma proteins (e.g. in plasmafiltration) and/or middle molecular weight blood toxins (e.g. in hemofiltration), suitably having molecular weight cutoffs of about 50,000 or above, e.g. 50,000 to 6,000,000. Suitable plasmafiltration and hemofiltration membranes include, for example, those known under the designations F-80 (50,000 m.w. cutoff, Fresenius USA, Inc., Walnut Creek, Calif.), Altrex 140 (70,000 m.w. cutoff, Althin Medical, Inc., Miami Lakes, Fla.)), CT190G (60,000 m.w. cutoff, Baxter, Deerfield, Ill.), and Plasmaflo AP-05H(L) (about 1,000,000 m.w. cutoff, Asahi Medical Co., Ltd., Tokyo, Japan). More preferred plasmafiltration or hemofiltration membranes will have pore sizes which transmit albumin or middle molecular weight molecules with selectivity over larger molecules, and thus will provide removal of toxins while minimizing potential interference with other blood functions. For example, the Plasmaflow AP-05H(L) plasma separator (0.5 square meters) has about a 5% rejection of albumin during unidirectional filtration, but about an 80% rejection of macroglobulins.

In connection with dialysis when used in the present invention, there are many dialyzer membranes which are known for use in dialyzing body fluids such as blood, and those skilled in the area will be readily able to select and utilize a suitable membranes in the present invention. One suitable membrane is a cellulosic membrane, particularly one composed of regenerated cuproammonium cellulose (Cuprophan).

In circumstances where only plasmafiltration or hemofiltration (and not dialysis) of the blood or other fluid is desired, the membrane in the dialysis instrument need not be a dialysis membrane, and thus may be one which is impermeable to blood and its components, e.g. a membrane formed from a suitable compliant plastic film. Moreover, where only plasmafiltration or hemofiltration is desired, the dialysis instrument need not be employed at all, and any means of circulating the sorbent suspension against the exterior of the hollow fiber membranes while passing the blood or other fluid through the interior of the membranes (with bidirectional flow of the blood or fluid across the membranes) will be suitable. For example, the hollow fiber membrane cartridge could have sorbent side connections to a container filled with sorbent suspension. While the sorbent suspension is circulated through the cartridge, for example by a roller pump, the pressure changes in the blood side (created automatically by roller pumps) would create the desired bidirectional flow of plasma or other fluid across the membranes. Such systems will provide high clearance of protein-bound or middle molecular weight toxins with great simplicity and low cost.

The inventive plasmafiltration or hemofiltration methods of the invention are advantageously performed in connection with a preferred, dialysis instrument including a parallel plate dialyzer and moving the sorbent suspension formulation in a counter-current mode by the direct application of alternating negative pressure and positive pressure on the dialysate side, as described in more detail in Examples 1 and 2 below. The preferred system also creates a slight back and forth motion of the sorbent suspension formulation, which agitates, locally mixes, and helps to prevent settling of the suspension.

Extracorporeal blood treatments of the invention can be used to safely and effectively-treat the coma and illness of hepatic failure and to improve a patient's clinical condition as evidenced by improved polysiologic and neurologic patient status. Methods of this invention can also be successfully used in treating drug overdose, even with highly-protein-bound drugs (i.e. drugs which are 75% or more protein bound). It is also expected that methods and devices of the invention will be effective in treating patients with renal failure, uremia, or other conditions benefited by removal of toxins from the blood. Further, plasmafiltration and/or dialysis methods of the invention can be used in hemofiltration to treat and remove toxins from the hemofiltration ultrafiltrate, and return the treated ultrafiltrate to blood. In this manner, the use of large volumes of sterile replacement fluid can be ameliorated or eliminated.

The invention will now be described with reference to the following specific Examples which are illustrative, and not limiting, of the invention.

EXAMPLE 1

Figure 1:
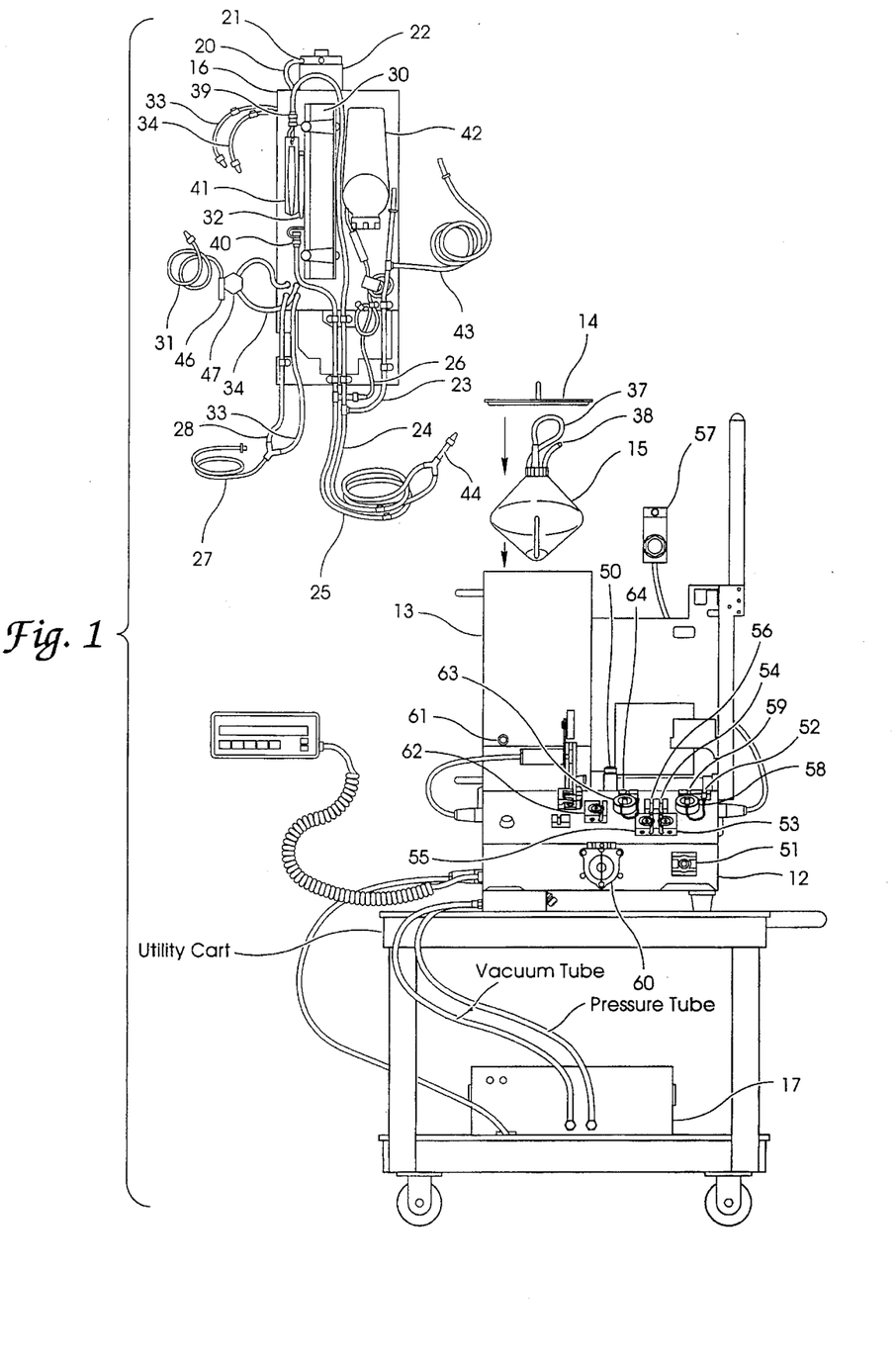
FIG. 1 is a perspective view of a preferred pressure/vacuum operated dialysis system which can be used in the invention.

Operation and Components of Preferred Vacuum/Pressure Operated Flow-Through Dialysis System FIG. 1 is a perspective view of a preferred dialysis system 11 sitting on a standard hospital cart, which can be used in methods of the invention. Generally, the preferred dialysis system 11 is similar in some respects to the dialysis instrument disclosed in my earlier U.S. Pat. No. 4,661,246 issued Apr. 28, 1987, which is hereby incorporated herein by reference in its entirely. However, to fill and empty the dialyzer of blood, the present system uses the direct application of pressure and vacuum to give positive and negative pressure changes in the dialysate. This increases the blood flow and enhances the mixing of the sorbent suspension formulation, as well as helps to maintain optimal chemical gradients across the dialysis membrane.

Figure 2:
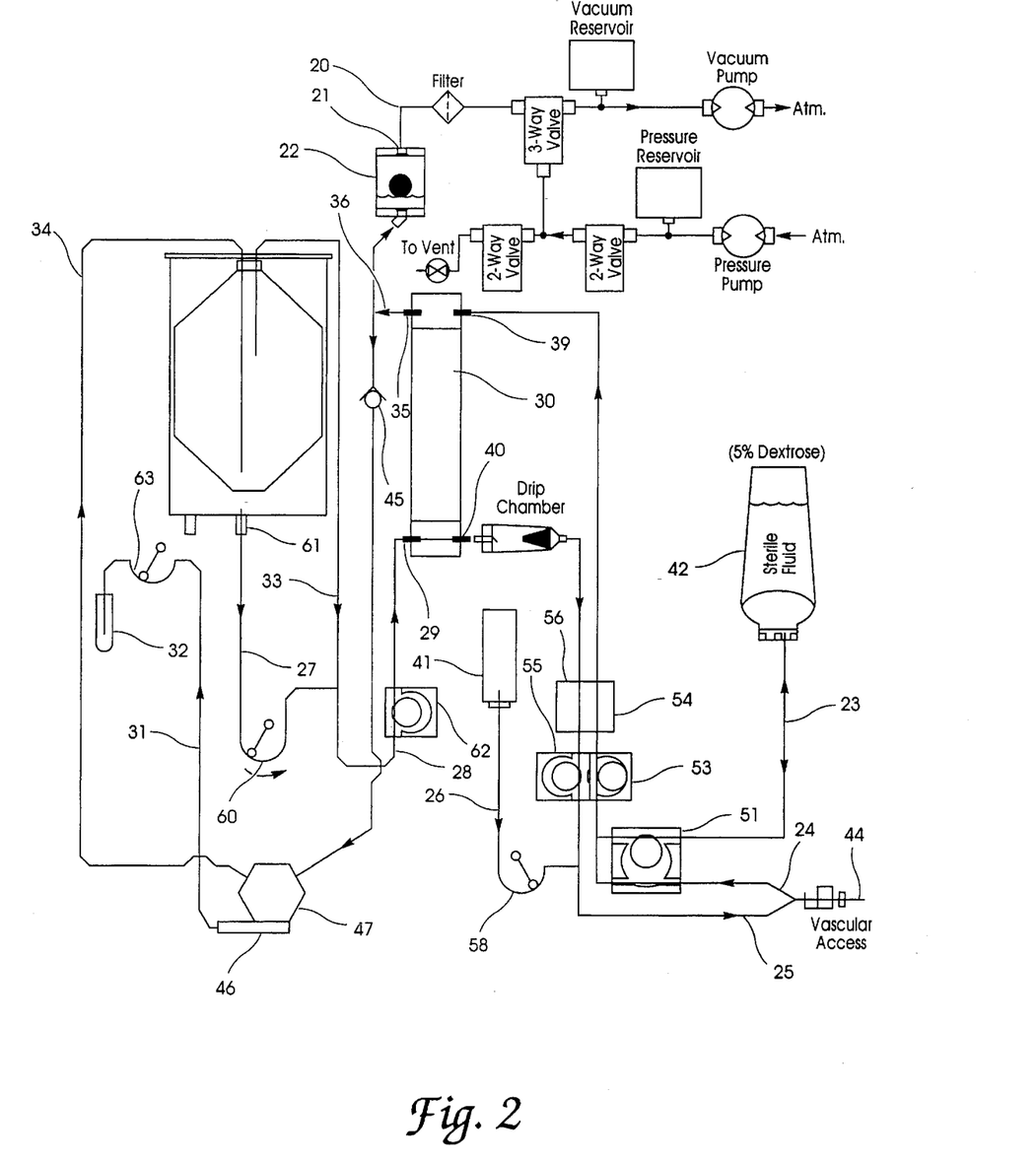
FIG. 2 is a schematic representation of the hydraulic system of the dialysis system of FIG. 1.
Figure 3A:
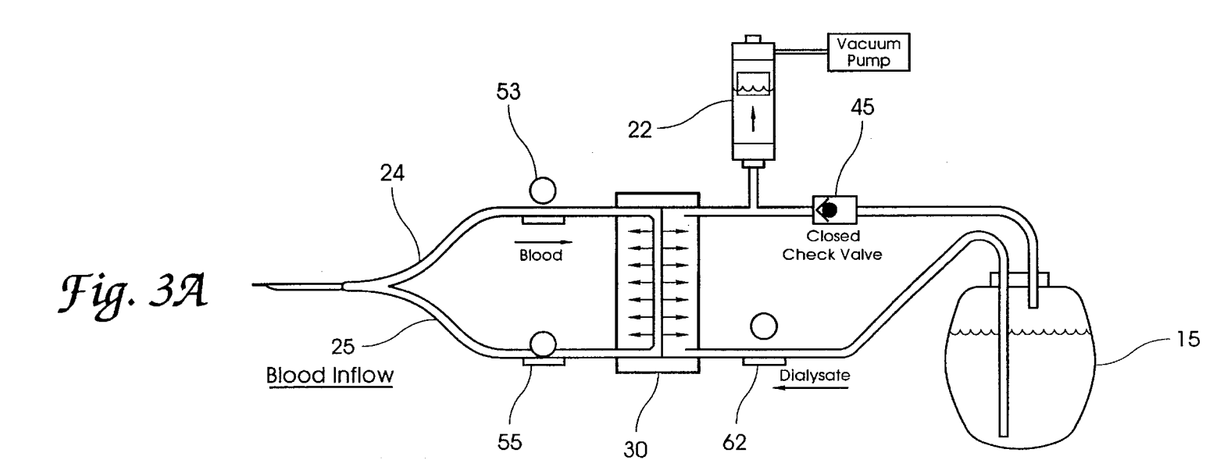
FIG. 3 is a schematic representation of the mechanics of operation of the preferred direct pressure/vacuum operated dialysis system of FIG. 1 during the first part of blood inflow (FIG. 3A) and during the remainder of blood inflow and blood outflow (FIG. 3B).
Figure 3B:
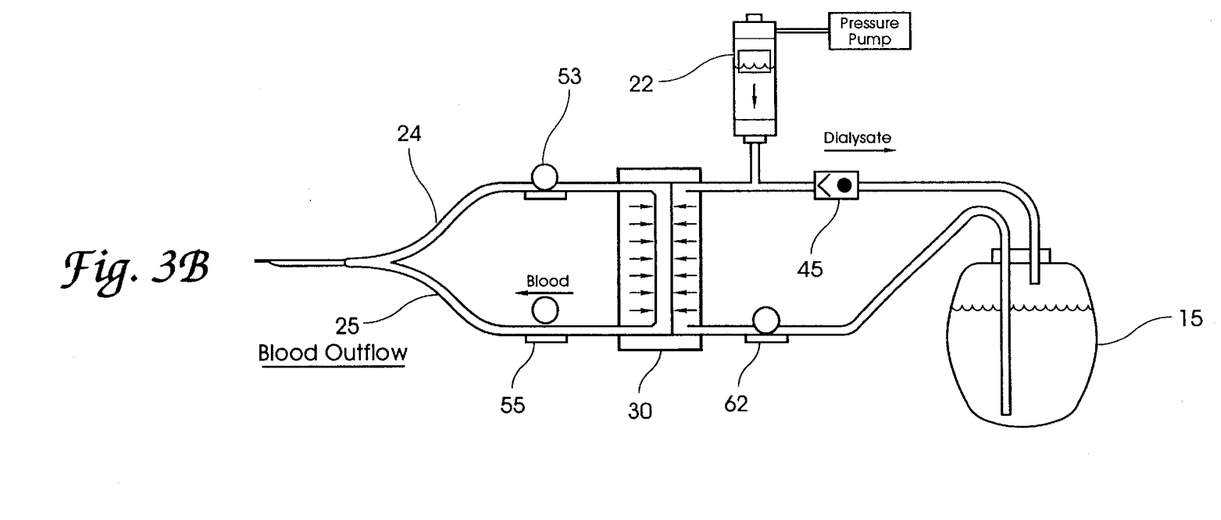

With continued reference to FIG. 1, the dialysis system 11 includes a machine base 12, reservoir tank 13 with cover 14, a sorbent bag 15 containing sorbent suspension materials, disposable pack 16 (including the plate dialyzer), and power supply 17 (providing vacuum, pressure, and DC power to the machine base). Referring now also to FIGS. 2 and 3, FIG. 2 is a hydraulic schematic of the dialysis system, and FIG. 3 provides in parts A and B a summary of the mechanics and hydraulics of operation of the system during blood inflow and outflow, respectively. Generally, in the following discussion, the numbers 20–47 will be used to designate components on the disposable pack 16, whereas numbers 50 and above will designate components of the machine base 12. In FIG. 1, the machine base 12 and disposable pack 16 are shown separated. Of course, in use together, the pack 16 is mounted to machine base 12 and their respective components assembled generally as follows.

Vacuum/pressure line 20 from top port 21 of accumulator 22 is connected to vacuum pressure port 50 on machine base 12 which feeds vacuum and pressure from the respective sources thereof are power supply 17. Prime tube 23 is seated into the upper side of prime/rinse clamp 51 and through prime fluid sensor 52. The blood inflow tube 24 is seated into the lower side of prime rinse clamp 51, blood inflow clamp 53 and the blood inflow sensor 54. The blood outflow tube 25 is seated into blood outflow clamp 55 and blood outflow sensor 56, and fluid level sensor 57 is placed onto accumulator 22. Reinfusate tube 26 is loaded into reinfusate pump 58 and reinfusate fluid sensor 59. Dialysate tube 27 (prior to the "Y" split) is loaded into dialysate pump 60 and its end connected to water port 61. Branch of dialysate tube 28 (after the "Y" split) which connects to the dialysate inlet 29 of dialyzer 30 is seated into dialysate-in clamp 62. Filtrate line 31 is loaded into filtrate pump 63 and into filtrate fluid sensor 64. Filtrate line 31 is also connected to filtrate disposal bag 32 which is vented. Three liters of sterile water are added to reservoir tank 13. Sorbent bag 15 is suspended from reservoir cover 14. Tubes 33 (leading to dialysate inlet 29) and 34 (leading to the exit port of accumulator 23 and also connected to dialysate outlet 35 via line 36) are connected to lines 37 and 38 provided on and leading into sorbent bag 15.

The following steps are conducted under sterile conditions. Blood inflow line 24 and blood outflow line 25 are connected to blood inlet 39 and blood outlet 40 of dialyzer 30, respectively. Reinfusate solution (e.g. $CaCl_2$ solution and appropriate amounts of KCl and/or NaCl solution) is injected into reinfusate bag 41. Reinfusate line 26 is connected to reinfusate bag 41 and a drip chamber in the line is partially filled. Prime tube 23 is connected to prime bottle 42 containing priming fluid, e.g. 5% dextrose. If desired, replacement fluid can be provided via fluid replacement line 43.

Figure 5A:
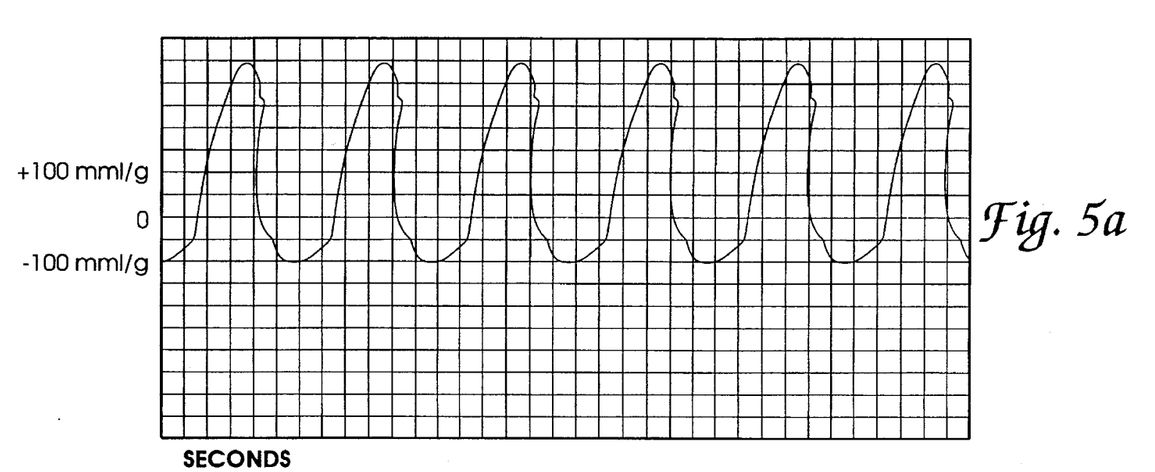
FIG. 5(a) shows the blood-side pressure curve between the system of FIG. 1 and the plasmafilter in the combined device of FIG. 4, during several inflow-outflow cycles.
Figure 5B:
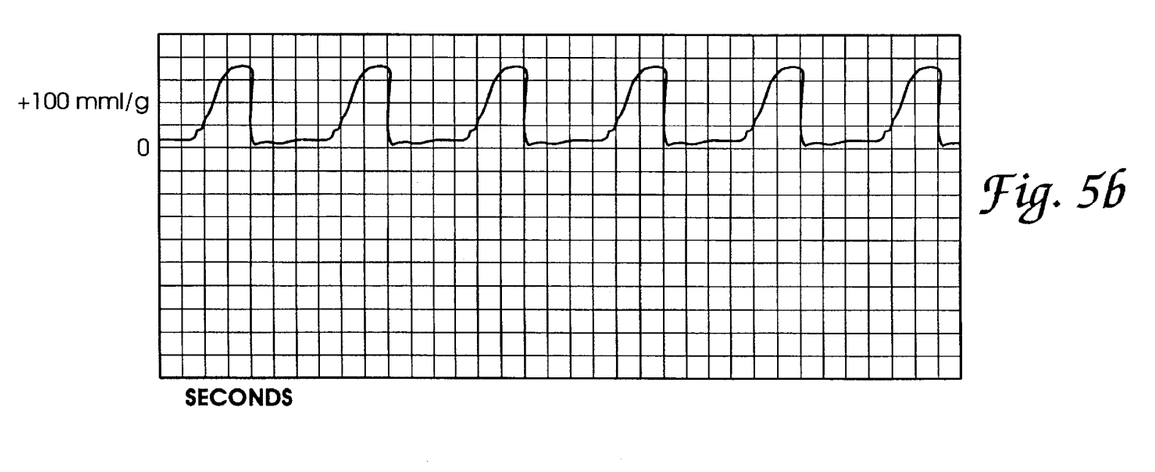
FIG. 5(b) shows the sorbent-side pressure curve within the plasmafilter membrane package of the combined device of FIG. 4. Mean blood-sorbent pressure difference is approximately zero.

Thus, after the above assembly, the blood inflow 24 and blood outflow 25 tubes pass from a single access line 44 through clamps 53 and 55 and optical monitors 54 and 56 to connect to the top 39 and bottom 40 openings of the blood side of the dialyzer 30. Cylindrical accumulator 22 attaches to the dialysate space at the top opening 35 of the dialysate side of dialyzer 30, and alternating strong vacuum (i.e. negative pressure) and modest positive pressure in accumulator 22 (provided by line 20 through port 21 above the fluid level) alternately draws dialysate into and expels dialysate from accumulator 22, which expands and compresses the membranes of dialyzer 30 (as illustrate by the arrows, FIG. 5), while the automatically controlled blood inflow and outflow clamps 53 and 55 assure that blood passes unidirectionally through the dialyzer 30, at an average rate of up to 250 ml/min (in 5 cycles). The ratio of inflow/outflow cycle times determines the ultrafiltration rate, from a minimum of about 200 ml/hr at a ratio of about 1.45, to about 600 ml/hr at a ratio of 2.45.

In the preferred dialysis system 11 utilized in the specific Examples, the dialyzer was a 1.6 $m^2$ COBE parallel screenplate dialyzer having dialysis membranes composed of regenerated cuproammonium cellulose (Cuprophan) and having a functional molecular weight cut-off of about 3000 daltons, i.e. only molecules of about 3000 daltons or less will pass through the membrane.

As opposed to many previously-known dialysis systems, the system used in the invention contains a sorbent suspension in the dialysate instead of merely a dialysis solution. Flow of the suspension is generally counter-current, and is both bidirectional between the accumulator 22 and dialyzer 30, and circular between the dialyzer 30 and sorbent reservoir 15.

Figure 4:
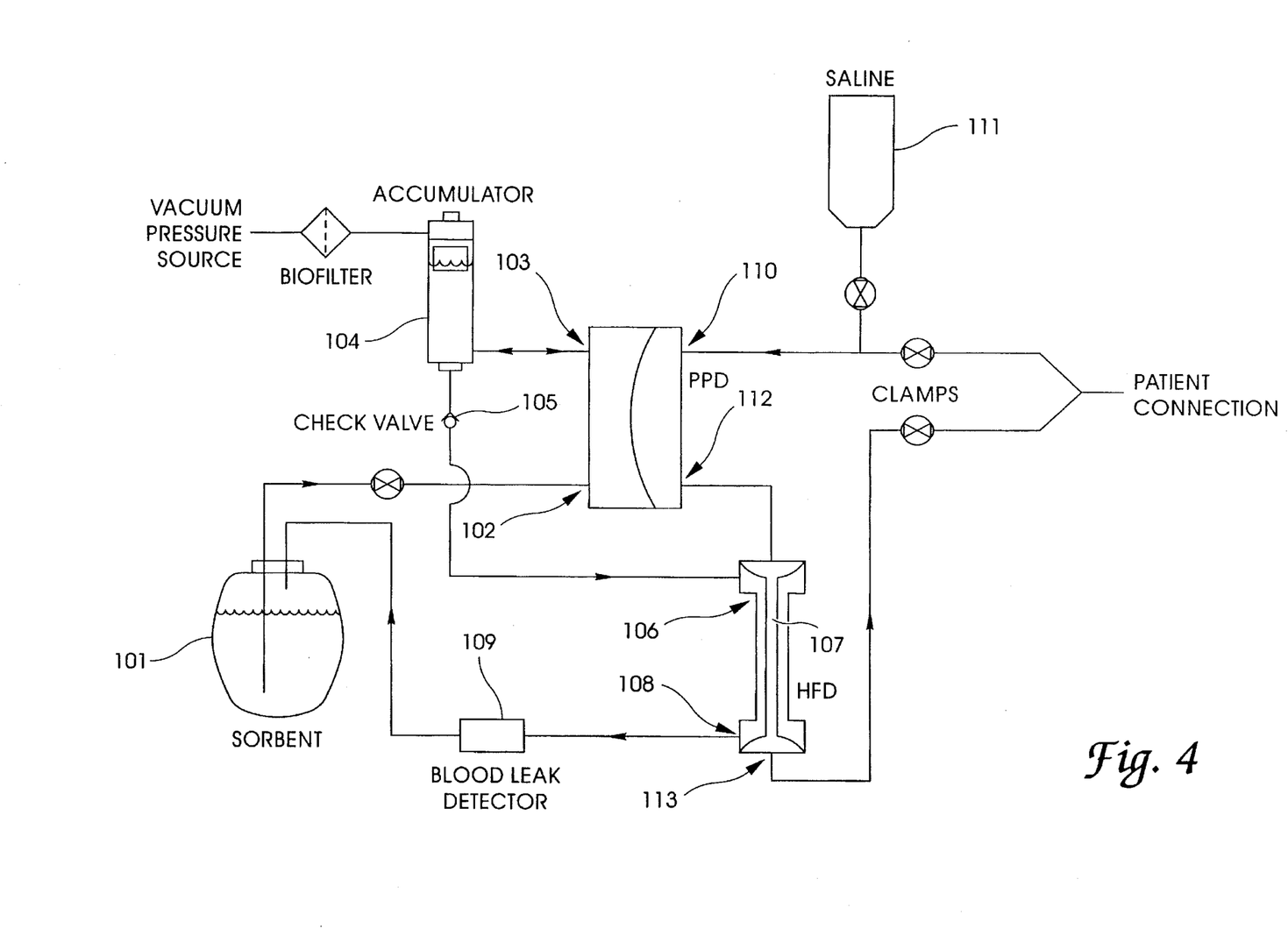
FIG. 4 is a schematic representation of the hydraulic circuit of a combined device incorporating the system of FIG. 1 in series with a hollow fiber plasmafilter.

In summary, during the first part of blood inflow (see particularly FIG. 3A), clamp 62 on the dialysate inflow line 33 opens, allowing sorbent suspension to flow from the sorbent reservoir 15 through the entire dialyzer 30, filling the accumulator 22 to the level of sensor 57. Clamp 62 then closes and remains closed during the remainder of inflow and all of outflow (see particularly FIG. 3B), when pressure in the accumulator 22 returns some suspension to the dialyzer 30 and passes some through one-way valve 45 to return to the reservoir 15 via dialysate return line 34. In typical operation, each minute, about 900 ml of sorbent suspension flows into accumulator 30 (in 5 cycles). 600 ml of sorbent suspension flows back into the dialyzer 30, and 300 ml flows from the accumulator 22 into the sorbent reservoir 15. This, along with the expansion and contraction of the dialyzer membranes, keeps the sorbent suspension well mixed at the dialyzer membrane surface. Typical blood side and dialysate side pressure, and the blood volume of the dialyzer over time during such operation are shown in FIG. 4. As can be seen, both the blood side and dialysate side pressures alternate between positive and negative pressure, while the spring action of the plate dialyzer membranes ensures that there is constantly a positive pressure gradient from blood side to dialysate side.

In one suitable system, sorbent bag 15 initially contains dry sorbent materials to which the system automatically adds 1.5 liters of sterile water from reservoir tank 13 via port 61 during priming. This operation is powered by dialysate pump 60. For the Examples given below, the sorbent materials in bag 15 were as follows:
140 grams powdered activated charcoal (300,000 square meters surface area, between 5 and 53 micron mean particle diameter, 70 micron maximum particle diameter)
80 grams cation exchanger (sodium polystyrene sulfonate, PSS, functional binding of 80 mEq).
1.5 grams Pluronic F68.
3.0 grams polyvinylpyrrolidone (PVP).
sodium bicarbonate and sodium chloride to result in physiologic starting concentrations in the dialysate sorbent suspension after priming (sodium=140 mEg/L, bicarbonate=35 mEg/L, chloride=105 mEg/L).

The priming fluid for the blood side of the dialysis system was one liter of 5% dextrose from container 42 attached to blood inflow tube 24 via tube 23. During priming, priming/rinse clamp automatically opens prime tube 23 while closing blood inflow tube 24. Priming fluid is thus pulled into the system rather than blood. Glucose passes across the membranes of the dialyzer 30, and 20 grams binds to the charcoal, while sodium chloride, and bicarbonate pass from the suspension into the priming fluid. During dialysis, glucose disassociates from the charcoal and returns to the patient (unless the patient's glucose is very high). A reinfusate of sterile calcium chloride and potassium chloride was pumped by reinfusate pump 58 from reinfusate container 41 through tube 26 into the outflow line 25 at a diminishing rate throughout the treatment, to offset removal by the cation exchanger.

The system also includes a variety of sensors to make operation safe, simple and highly automated, including:
a scale to weigh the entire top of the machine, to measure volumes ultrafiltered from and returned to the patient;
blood sensors (54 and 56) to measure foam, bubbles, particles of blood in the inflow and outflow lines 24 and 25, and to measure flow rate-on the inflow line 24;
hemoglobin sensor 46 to chemically detect hemoglobin within the sorbent suspension if there is a membrane blood leak. For this function, a filtrate collector 47 provides a solid-free sample of the dialysate fluid to hemoglobin sensor tape which changes color if hemoglobin is present. The tape is automatically wetted with samples of dialysate, advanced and monitored for color change by a reflectometer. The wetting of the tape is controlled by filtrate pump 63 which further pumps excess filtrate via tube 31 into collection container 32.
empty line sensors on all fluid-filled lines;
temperature sensor for fluid in the reservoir tank 13 surrounding the sorbent bag 15 (optimally heated to about 37° to 40° C. by heating elements also provided in the machine).

The computers of the system automate many of the steps of treatment, including:
priming of the machine, observing lines to determine that all air is removed;
returning fluid to the patient when desired final weight is obtained or of command (for the latter, automatically adjusting ultrafiltration to reach desired final weight).
rinsing the dialyzer and blood lines at the end of treatment; and
recording, storing and transferring data concerning progress of each treatment.

EXAMPLE 2

Combined Dialysis/Plasmafilter or Hemofilter Device

FIG. 4 provides a schematic diagram showing the hydraulics of a combined dialysis/plasmafilter device in accordance with the invention. As shown, the device incorporates a parallel plate dialyzer ("PPD") connected in series with a hollow fiber membrane device ("HFD"). In this regard, it will be understood that the present invention is not limited to such a combined device, and that the HFD could be used as the sole agent for treatment of the blood. Further, when used in combination with the PPD, the HFD can be incorporated in any suitable location within the sorbent circulation side of the PPD. Preferably, the HFD will be incorporated to as to achieve high bidirectional plasma flow across the membranes of the HFD, with a net flow of about zero to prevent increasing sorbent volume (which would increase the volume of distribution for albumin and increase loss of albumin from the patient). The HFD is also desirably incorporated so as to provide blood treatment rates over 150 ml/min., to allow high filtration rates across the membranes and permit high clearance of protein-bound or middle molecular weight substances.

In the illustrated arrangement, the HFD is connected in series with the PPD such that sorbent suspension exiting the sorbent reservoir first passes through the PPD and then the HFD. More particularly, sorbent is first drawn from sorbent bag 101 and into sorbent inlet 102 of the PPD. Sorbent exits sorbent outlet 103 and is drawn into accumulator reservior 104, whereafter it is expelled from accumulator reservoir 104 and passes through check valve 105. The sorbent suspension then passes into HFD inlet 106 and through the outer chamber of the HFD, thus passing into contact with exterior surfaces of the hollow fibers 107 in the HFD package. Sorbent suspension exits the HFD from outlet 108, and passes through blood leak detector 109 and back into sorbent bag 101. The HPD can be suitably operated as described in Example 1 above. In this manner, the sorbent suspension is also effectively agitated and mixed at the surface of the membranes in the HFD. Additionally, when alternating positive and negative pressure is applied to the sorbent circuit via the accumulator reservoir 104, check valve 105 prevents negative pressure from being applied to the HFD sorbent side, and creates only intermittent positive pressure (FIG. 5(b)). In this system, the blood-side (see FIG. 5(a)) and dialysate-side pressures vary with each cycle, but are balanced on average, thus creating a bidirectional flow in each cycle but with zero net filtration (there is net sorbent to blood filtration in the HFD, offsetting ultrafiltration of the PPD, several hundred ml/hr.). On the blood side, blood passes from the patient access and into blood inlet 110 of the PPD, with the intermediate addition of saline from reservoir 111. Where a dialysis membrane (as opposed to an impermeable membrane) is installed in the PPD, the blood is dialyzed in the PPD as described above. Blood then exits the PPD through outlet 112 and passes into interior channels of the follow fibers of the HFD (commercial HFD devices have a package including a plurality of hollow fiber membranes). At this point, the alternating positive and negative pressure applied of the sorbent side causes a bidirectional flow of plasma across the hollow fiber membranes, that is, the blood plasma exits and then re-enters the hollow fiber membranes. While exterior of the hemofilter or plasmafilter membranes, middle molecular weight toxins and/or plasma proteins, including proteins to which toxic substances are bound, come into contact with the sorbent suspension. The toxic substances are adsorbed to the adsorbents, and in the case of plasmafiltration, the proteins, now free of toxins, are passed back into the hollow fiber membranes. Thus, effective plasmafiltration or hemofiltration of the blood is achieved as the blood passes through the HFD. Blood exits the HFD via outlet 113, and is returned to the patient through the patient access.

The pressures of the blood-side and sorbent-side will vary with the particular HFD devices employed. Thus, with a particular HFD device, in vitro tests can be done to measure filtration rate, and the vacuum and pressure operating the system will be adjusted to attain zero net filtration. Moreover, to optimize blood flow, adjustments to the ratio of inflow/outflow times can be made. The combined PPD/HFD system will, like the system described in Example 1, measure the rate of ultrafiltration by weighing the entire top of the device, including the sorbent bag. But, since the goal is net ultrafiltration of about zero, there is no need for the long inflow times of the system of Example 1. Better blood flow will be obtained using approximately equal inflow and outflow times. During in vitro tests, for example with pig blood, the driving pressures can be adjusted as above, and the net blood flow determined (by change of weight of the 3 liter container during each cycle). The inflow-outflow times can then be adjusted to give maximum blood flow. Preferably, the 200–225 ml/min average blood flow of the system of Example 1 is maintained.

EXAMPLE 3

Blood Treatment With Dialysis/Plasmafilter or Hemofilter Device

Figure 6A:
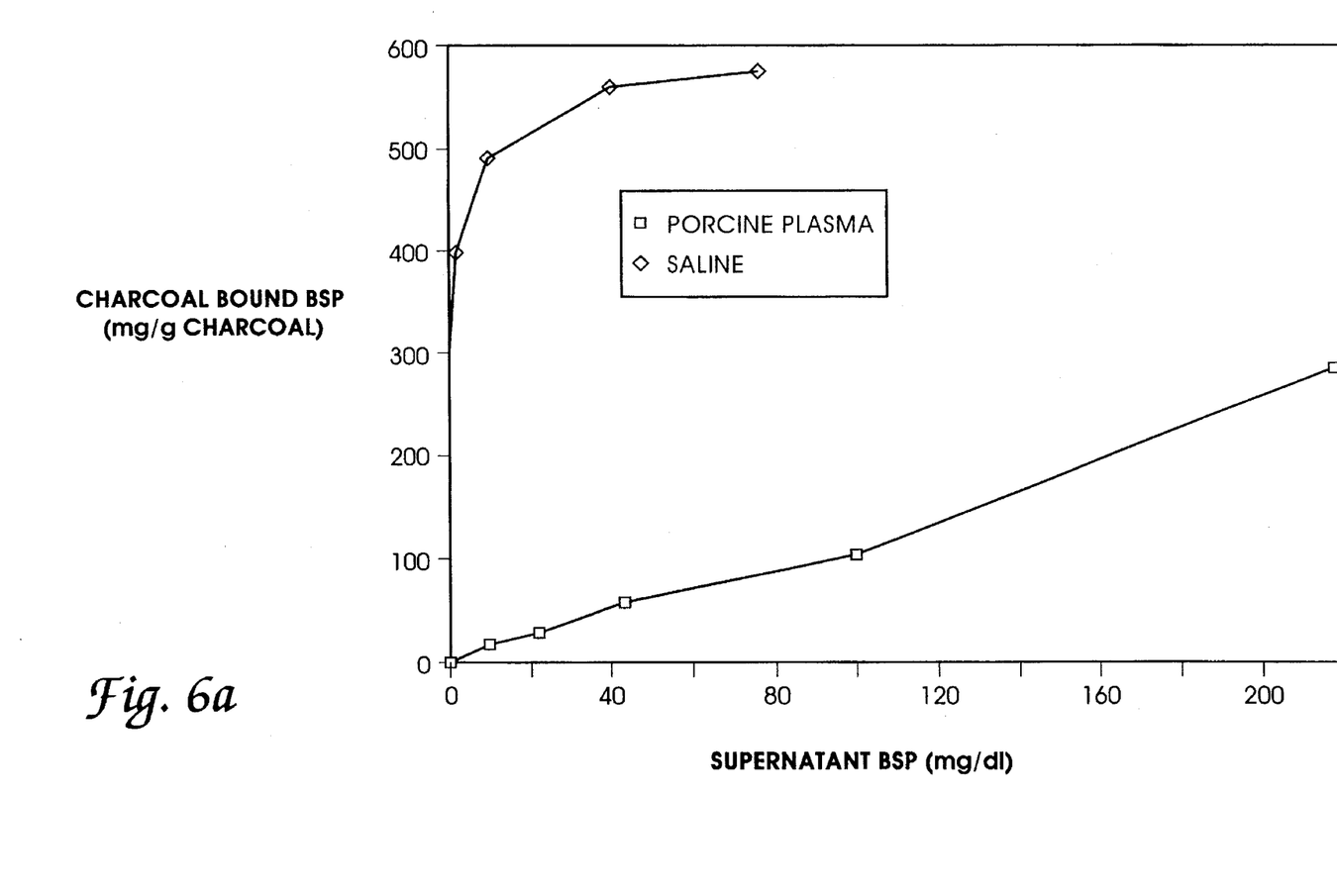
FIG. 6(a) shows a Langmuir isotherm for binding of bromsulphthalein (BSP) from saline (top line) and from porcine plasma (bottom line) to which it was first bound to charcoal.
Figure 6B:
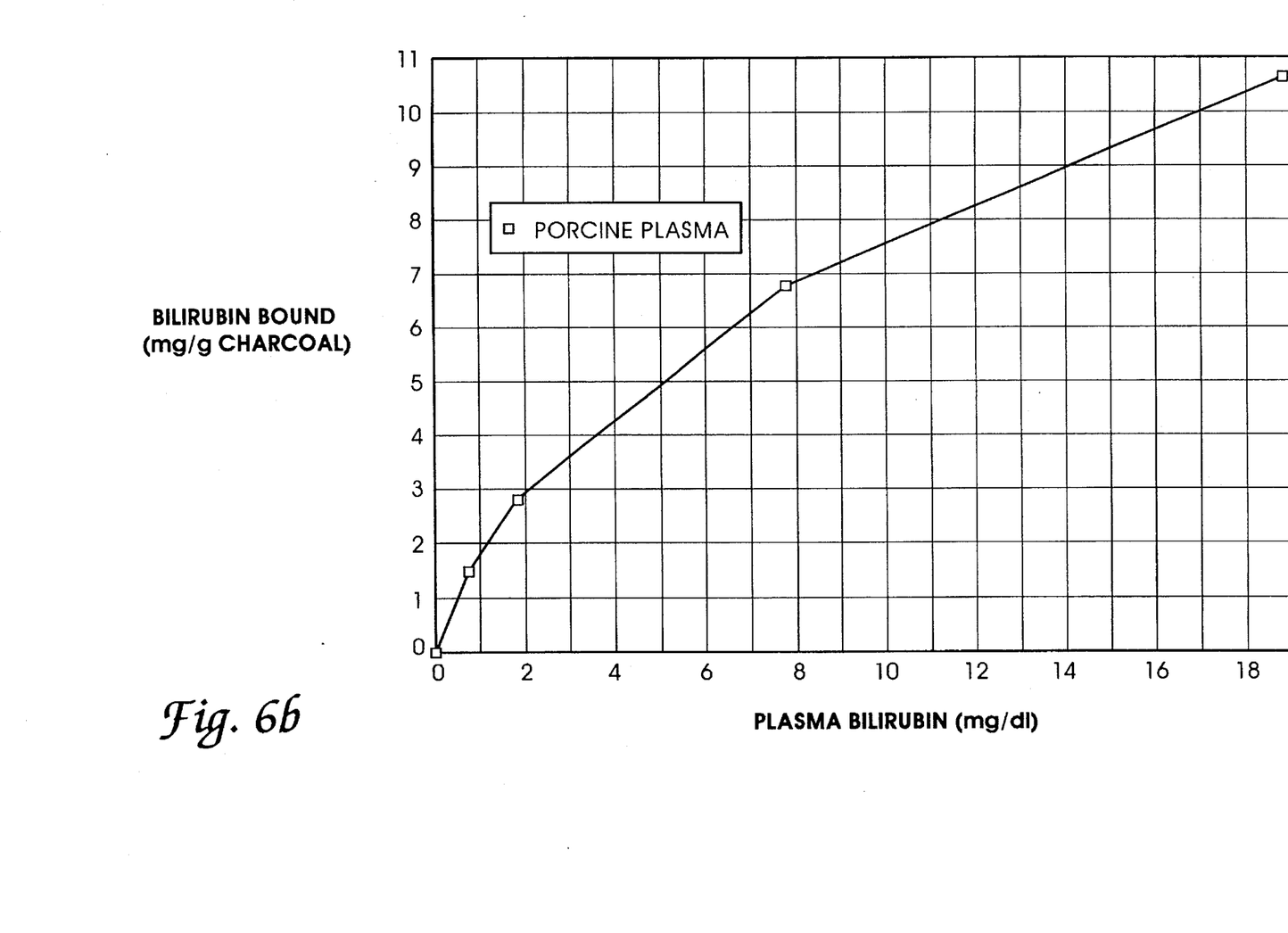
FIG. 6(b) shows a Langmuir isotherm for binding of unconjugated bilirubin from porcine plasma to which it was first bound to charcoal.

Charcoal has the capacity to very effectively adsorb middle molecular weight molecules and protein-bound toxins (see, e.g., FIGS. 6(a) and 6(b) which provide Langmuir isotherms of the adsorption of BSP from plasma and saline and of bilirubin from plasma). In the following studies, the PPD/HFD device described in Example 2 was used to determine clearance rates of some protein-bound and middle molecular weight substances from blood. 3 liters of fresh pig blood were spiked with various substances (Shown in Table 1 below), and the blood was treated using the PPD/HFD device. During several hours of treatment, the blood was continuously infused with the substances at a rate designed to maintain a constant concentration (calculated by the predicted clearance of the system). The clearances were then determined by dividing the rate of infusion by the steady-state concentration of the substance. If the blood volume changed, then the change was included in the calculation of clearance. The results are shown in Table 1, in which "Great"=creatinine, "Bili"=bilirubin, BSP, and "Vanco"=vancomycin. Among these, creatinine is a small, non-protein bound substance, bilirubin, Elavil and BSP are small, highly protein-bound molecules, and vancomycin is a middle molecular weight:., non-protein bound substance.

TABLE 1

| | BLOOD FLOW AND CLEARANCES (ml/min) | | | | | |
|---|---|---|---|---|---|---|
| Membrane | Ave Qb. | Creat | Bili | BSP | Elavil | Vanco |
| PPD only | 200 | 140 | 0 | 0 | 12 | 0 |
| F-80 | 150 | 130 | 12 | n/a | 40 | — |
| Altrex 140 (70K) | 180 | 130 | 5 | n/a | — | — |
| Althin* | 140 | 90 | 5 | n/a | 19 | 37 |
| CT190G | 160 | 85 | 0 | — | — | 62 |
| Plasmaflo AP-05H(L) | 140 | 95 | 43 | n/a | n/a | 35 |

— (dash) = no data
n/a = data not currently available
*developmental filter from Althin Medical, Inc., m.w. cutoff = 100,000.

As can be seen, use of the HFD can provide significant increases in the clearance of middle molecular weight and protein-bound substances, and can be used in connection with the PPD to provide effective overall clearance of small and larger substances, both protein-bound and non-p rote in-bound.

While the invention has been illustrated and described in detail in the drawings and foregoing description, the same is to be considered as illustrative and not restrictive in character, it being understood that only the preferred embodiments leave been shown and described and that all changes and modifications that come within the spirit of the invention are desired to be protected.

What is claimed is:

1. A filtration process for removing blood toxins, comprising:

passing a fluid containing protein bound and/or middle molecular weight blood toxins through the interior of a hollow fiber membrane;

during said passing, circulating a sorbent suspension against exterior surfaces of the hollow fiber membrane;

during said passing and circulating, applying intermittent pulses of positive pressure to said sorbent suspension so that the fluid or a fraction thereof alternately exits and re-enters the interior of the hollow fiber membrane, wherein said fluid or fraction which exits the interior of the hollow fiber membrane contains the protein bound and/or middle molecular weight toxins which contact said sorbent suspension so as to effectuate removal of said toxins from said fluid and delivery of said toxins into said sorbent suspension.

2. The process of claim 1, wherein said hollow fiber membrane is a hemofiltration membrane, whereby middle molecular weight toxins are removed from said fluid.

3. The process of claim 1, wherein said hollow fiber membrane is a plasmafiltration membrane, whereby middle molecular weight toxins and protein-bound toxins are removed from said fluid.

4. The process of claim 3, wherein said plasmafiltration membrane transmits albumin with selectivity over larger proteins.

5. The process of claim 1, wherein said fluid is blood.

6. A blood dialysis device which comprises:

a hollow fiber membrane;

a pump fluidly connected to the interior of said hollow fiber membrane and adapted to pass a fluid containing middle molecular weight and/or protein-bound blood toxins through the interior of said hollow fiber membrane;

a chamber surrounding said hollow fiber membrane, said chamber further being fluidly connected to a supply of sorbent suspension;

a pump adapted to circulate said sorbent suspension through said chamber and against exterior surfaces of said hollow fiber membrane; and means for causing said fluid or fractions thereof passing through the interior of the follow fiber membrane to alternately exit and re-enter said interior.

7. The device of claim 6, wherein said hollow fiber membrane is a hemofiltration membrane.

8. The device of claim 6, wherein said hollow fiber membrane is a plasmafiltration membrane.

9. The device of claim 8, wherein said plasmafiltration membrane transmits albumin with selectivity over larger proteins.

10. The device of claim 6, further comprising a dialysis instrument adapted to dialyze said fluid fluidly connected in series with the interior of said hollow fiber membrane.

* * * * *

UNITED STATES PATENT AND TRADEMARK OFFICE
CERTIFICATE OF CORRECTION

PATENT NO. : 5,536,412
DATED : July 16, 1996
INVENTOR(S) : Stephen R. Ash

It is certified that error appears in the above-indentified patent and that said Letters Patent is hereby corrected as shown below:

In col. 5, line 61, please delete "oilier" and insert in lieu thereof --other--.

In col. 8, line 14, please delete "are" and insert in lieu thereof --in--.

In col. 9, lines 52-53, please delete all occurrences of "Eg" and insert in lieu thereof --Eq--.

In col. 10, line 9, please delete the hyphen in between the words "rate" and "on".

In col. 10, line 30, please delete "of" and insert in lieu thereof --on--.

In col. 11, line 8, please delete "HPD" and insert in lieu thereof --PPD--

In col. 11, line 22, please begin a new paragraph starting with the words "On the blood side,".

In col. 11, line 32, please delete "of" (first occurrence) and insert in lieu thereof --on--.

In col. 12, line 25, please delete "Great" and insert in lieu thereof --Creat--.

UNITED STATES PATENT AND TRADEMARK OFFICE
CERTIFICATE OF CORRECTION

PATENT NO. : 5,536,412
DATED : July 16, 1996
INVENTOR(S) : Stephen R. Ash

It is certified that error appears in the above-indentified patent and that said Letters Patent is hereby corrected as shown below:

In col. 12, line 29, please delete ":." after the word "weight".

In col. 12, line 57, please delete "leave" and insert in lieu thereof --have--.

In col. 14, line 12, please delete "follow" and insert in lieu thereof --hollow--.

Signed and Sealed this

Twenty-sixth Day of August, 1997

Attest:

BRUCE LEHMAN

*Attesting Officer*     *Commissioner of Patents and Trademarks*